(12) United States Patent
Cookingham et al.

(10) Patent No.: US 6,639,999 B1
(45) Date of Patent: Oct. 28, 2003

(54) APPARATUS FOR ASSESSING OVERALL QUALITY OF HARDCOPY IMAGES

(75) Inventors: Robert E. Cookingham, Webster, NY (US); Brian W. Keelan, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/434,140

(22) Filed: Nov. 4, 1999

(51) Int. Cl.$^7$ ................................................ G06K 9/00
(52) U.S. Cl. ..................... 382/112; 382/141; 382/218
(58) Field of Search .................. 382/100, 181, 382/218, 219, 263, 141, 147, 112; 356/237.1; 430/20; 347/19

(56) References Cited

U.S. PATENT DOCUMENTS

| | | | | |
|---|---|---|---|---|
| 4,023,911 A | * | 5/1977 | Julesz et al. ............. | 356/237.1 |
| 5,400,667 A | | 3/1995 | Feng et al. ................ | 73/865.8 |
| 5,447,811 A | * | 9/1995 | Buhr et al. ................. | 430/20 |
| 5,526,113 A | * | 6/1996 | Lengyel et al. .......... | 356/124.5 |
| 5,600,574 A | * | 2/1997 | Reitan ........................ | 702/185 |
| 5,687,250 A | * | 11/1997 | Curley et al. ............. | 382/112 |
| 5,712,921 A | * | 1/1998 | Zabele ....................... | 382/112 |
| 5,754,674 A | * | 5/1998 | Ott et al. ................... | 382/112 |
| 5,778,088 A | * | 7/1998 | Stringa ...................... | 382/112 |
| 5,963,654 A | * | 10/1999 | Prakash et al. ............ | 382/112 |
| 5,999,636 A | * | 12/1999 | Juang ........................ | 382/112 |
| 6,275,600 B1 | * | 8/2001 | Banker et al. ............. | 382/112 |
| 6,292,584 B1 | * | 9/2001 | Dulaney et al. ........... | 382/151 |
| 6,307,980 B1 | * | 10/2001 | Quacchia ................... | 382/268 |
| 6,360,005 B1 | * | 3/2002 | Aloni et al. ............... | 382/148 |
| 6,363,162 B1 | * | 3/2002 | Moed et al. ............... | 382/112 |
| 6,477,266 B1 | * | 11/2002 | Asar ........................... | 382/147 |

OTHER PUBLICATIONS

Zwick et al, RMS Granularity: Determination of Just Noticeable Differences, SMPTE Journal, vol. 86, Jun. 1977, pp. 427–430.

Bartleson et al, Optical Radiation Measurements, Academic Press, 1984, pp. 441–489.

* cited by examiner

*Primary Examiner*—Jayanti K. Patel
(74) *Attorney, Agent, or Firm*—Raymond L. Owens

(57) ABSTRACT

An apparatus for producing a numerical representation of perceived overall image quality of a test image includes a viewing support for mounting the test image; a reference image holder disposed relative to the test image on the viewing support, and a source of light for uniformly illuminating the test image and the reference image disposed at the viewing position for viewing by a user. The apparatus can also include a guide with a track.

3 Claims, 3 Drawing Sheets

FIG. I

APPARATUS FOR ASSESSING OVERALL QUALITY OF HARDCOPY IMAGES

CROSS REFERENCE TO RELATED APPLICATION

Reference is made to commonly-assigned U.S. patent application Ser. No. 09/433,898 filed Nov. 4, 1999 entitled "Method for Assessing Overall Quality of Digital Images" by Cookingham et al, the disclosure of which is incorporated herein.

FIELD OF THE PRESENT INVENTION

The present invention relates to the visual assessment of a hardcopy image to yield a numerical representation of the perceived overall image quality.

BACKGROUND OF THE PRESENT INVENTION

Most perceptual experiments in the past have reported results in terms of ratings scales that are indefinite or unstable, e. g. in terms of adjective descriptors such as "good" or "fair". This limits the value of these experiments to their immediate conclusions, and prevents subsequent application of the results to new problems. In addition, standard psychophysical test methods such as paired comparison, category sort, etc. are subject to one or more of the following problems (see Part II of C. J. Bartleson and F. Grum, "Optical Radiation Measurements", Vol. 5, Academic Press, New York, 1984). Examples of problems found in standard methods include: low precision; stimuli-induced range effects; quality range characterized; and difficulty of inference of perceptually relevant differences.

U.S. Pat. No. 5,400,667, teaches that a reference image series varying in one perceptual attribute and calibrated in terms of a corresponding objective measurement may be used to perform a visual assessment of the objective measurement value associated with a test sample by identifying which member of the reference image series is most similar in the appearance of the varying perceptual attribute. For example, a reference image series varying in resolution in a known fashion can be used to perform a visual assessment of the resolution of a test image. A small number of adjective descriptors (e. g. "good" or "fair") are associated with the measurement scale to provide a crude perceptual characterization. For example, a resolving power of 1 cycle/mm might be considered "poor" and 5 cycles/mm "good". While the method of U.S. Pat. No. 5,400,667 can reduce the magnitude of the examples of problems mentioned above, it is still deficient in a number of respects as set forth below:

(1) It provides a measure of only a single perceptual attribute, namely, the perceptual attribute that varies within the reference image series. Practical imaging systems produce images with many combinations of perceptual attributes, so that customer satisfaction will be only partially correlated with any single perceptual attribute. What is of much greater relevance is the overall image quality. The term "overall image quality" means a subjective determination by a user of an image reflecting the relative acceptability of such image to the user. For example, if a test image had "good" resolution but "poor" color quality, matching the appearance to a reference image series varying in resolution according to the method of U.S. Pat. No. 5,400,667 would yield an estimate of the objective measurement value of resolving power (approximately 5 cycles/mm) and an associated adjective descriptor of "good". However, the overall image quality of the test image would be lower than this due to the poor color quality.

(2) The adjective descriptors provide only a very coarse classification and are not quantitative in nature. The same adjective descriptors are interpreted to mean different things by different people, and the application of adjective descriptors changes over time. The differences in quality between adjacent adjective descriptors is not uniform and is larger than the differences that need to be characterized in product design.

(3) The method also does not include a provision for individual calibration of reference image series depending on their scene content. It is well known that scene content significantly affects the impact of different attributes on overall image quality. For example, the overall image quality of complex scenes with considerable fine detail is relatively less affected by the presence of a given amount of noise, as determined by objective measurement values, than is that of simpler scenes with large areas of slowly changing color (e. g. blue sky; see D. M. Zwick and D. L. Brothers, "RMS Granularity: Determination of Just-Noticeable-Differences", SMPTE 86, pp. 427–430, 1977).

(4) U.S. Pat. No. 5,400,667 discloses reference image series spanning the range from "very poor" to "very good", which may not be a good match to the range of test images to be evaluated in a particular application.

(5) The method does not identify a preferred relationship among the increments of change between the adjacent members of the reference image series, yet this affects the speed and precision of the visual assessments.

(6) U.S. Pat. No. 5,400,667 does not discuss requirements for the viewing environment in which the visual assessment is made; however, this must be carefully controlled to obtain accurate and reproducible results.

(7) The method does not include a provision for evaluation and correction of user bias due to, for example, a tendency in the visual assessment to avoid approaching end numbers in the reference image series.

SUMMARY OF THE PRESENT INVENTION

It is an object of the present invention to provide an apparatus for measuring perceived overall image quality of a test image in terms of a numerical scale representing overall image quality.

This object is achieved by Apparatus for producing a numerical representation of perceived overall image quality of a test image, comprising:

(a) a viewing support for mounting the test image;

(b) a reference image holder disposed relative to the test image on the viewing support and mounting a reference image series that differ from each other by at least one perceptual attribute, wherein each reference image has a corresponding numerical representation indicating overall image quality, the reference image holder being movable so that any one of the reference images can be disposed in a viewing position adjacent to the test image; and (c) a source of light for uniformly illuminating both the test image and reference image disposed at the viewing position for viewing by a user, so that a user can compare any reference image with the test image at the viewing position for determining the relationship of the overall image quality of the most similar reference images to that of the test image and the numerical representation of the test image are inferred and recordable.

The present invention incorporates a reference image series that is calibrated against a standard numerical scale of overall image quality and is presented in a fashion that facilitates direct comparison of any of the reference images with the test image under matched viewing conditions. The present invention permits visual assessment of the overall image quality of the test image compared to the most similar reference images from the reference image series. The present invention also permits untrained personnel to perform calibrated visual assessments of overall image quality with accuracy and precision comparable to that of highly trained professionals using standards of limited availability.

Additional advantages of the present invention include:

(1) The present invention provides a measure of overall image quality rather than a single perceptual attribute, the former being more strongly correlated with customer satisfaction.

(2) The present invention produces a numerical representation of overall image quality that may be calibrated to an established scale with desirable properties such as associated physical standards, known increments of perceptual relevance, and general acceptance.

(3) The present invention provides for individual calibration of reference image series based on different reference scenes. This improves the accuracy of the method by accounting for the well-known variation of the effect of a perceptual attribute on overall image quality due to scene content (see D. M. Zwick and D. L. Brothers, "RMS Granularity: Determination of Just-Noticeable-Differences", SMPTE 86, pp. 427–430, 1977).

(4) The present invention permits optimization of the number of members in the reference image series and the increments of change between them, taking into account the range of overall image quality of the test images and the required precision. Proper choice of these properties minimizes the time spent by the user to produce numerical representations of a given required precision.

(5) The present invention creates a viewing environment in which important viewing factors such as viewing distance, viewing angle, illumination level, user adaptation level and flare light can be precisely matched between the displayed test image and the displayed reference image. This improves the accuracy of visual assessments by eliminating sources of bias. The present invention further permits such viewing factors to be fixed at specific prescribed values, which is important when these factors affect the appearance of perceptual attributes of either the test images or the reference images.

(6) The present invention permits correction for user and experimental biases by including within the test images one or more images that are identical to members of the reference image series either in terms of appearance or objective characteristics.

The performance of the present invention has been tested in several ways that demonstrate its effectiveness. First, the uncertainty in a single assessment has been measured and found to be two to four times smaller than standard psychophysical methods such as magnitude estimation and category sort problems (see Part II of C. J. Bartleson and F. Grum, "Optical Radiation Measurements", Vol. 5, Academic Press, New York, 1984). This uncertainty is comparable to that achieved by highly trained professionals using cumbersome standards. Second, the accuracy and precision of results obtained when the test image depicts a different scene than that of the reference series have been found to be just as good as in the case where the scenes are matched, a surprising result. This permits test images depicting arbitrary scenes to be evaluated without loss of performance.

DETAILED DESCRIPTION OF THE PREFERRED EMBODIMENTS

The present invention has been described in detail with particular reference to certain preferred embodiments thereof. but it will be understood that variations and modifications can be effected within the spirit and scope of the present invention.

The present invention improves upon existing apparatus by incorporating a reference image series that is calibrated against a standard numerical scale of overall image quality and is presented in a fashion that facilitates direct comparison of any of the reference images with the test image under matched viewing conditions, permitting visual assessment of the overall image quality of the test image compared to the most similar reference images from the reference image series.

Figure 1:
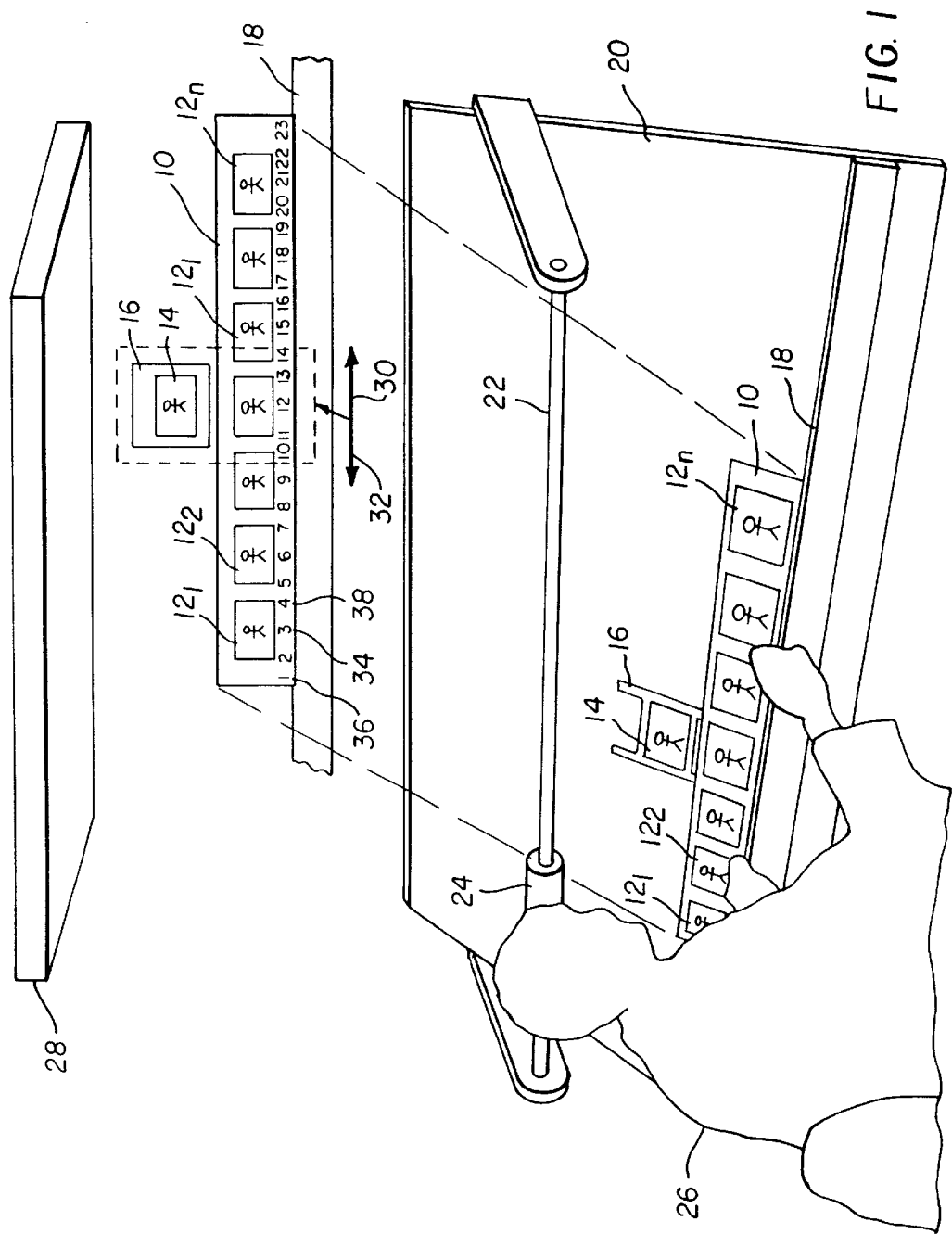
FIG. 1 is a pictorial representation of the viewing environment and apparatus used in performing visual assessments with the apparatus of the present invention, the reference image holder being shown in more detail and in an exploded fashion.

The apparatus for producing a numerical representation of overall image quality of a test image in accordance with a preferred embodiment of the present invention can be implemented using the apparatus and viewing environment shown in FIG. 1. The viewing environment consists of a reference image holder 10 capable of holding "n" reference images $12_1, 12_2, \ldots 12_i, \ldots 12_n$. The reference images 12 are all of the same scene and vary in overall image quality due to the presence of a degrading perceptual attribute. In the preferred embodiment of the present invention, the reference image holder 10 is constructed in a laminated structure from two thin sheets of a neutral colored polymer material that contain milled slots for insertion of the reference images 12. A fixture referred to as the test image holder 16 for holding and positioning a test image 14 is positioned directly in front of a user 26. A reference image holder guide 18 runs horizontally and contains a groove permitting easy slidable translation of the reference image holder 10 both right and left 32. The reference image holder 10 mounts a reference image series 12 that differ from each other in at least one perceptual attribute. The reference image holder 10 is movable so that any one of the reference images 12 can be disposed in a viewing position adjacent to the test image 14. In the preferred embodiment of the present invention, the user 26, slides the reference image holder 10 right and left to position directly below the test image 14 the reference image $12_i$ that most closely matches the overall image quality of the test image 14, or alternatively if one of the reference images 12$_i$ is not of exactly the same overall image quality, slides the reference image holder 10 such that the two reference images 12$_i$ and 12$_{i+1}$ that bracket the test image 14 in overall image quality are below the test image 14. At the time a final visual assessment is made of the overall image quality of a test image, both the test image 14 and the reference image 12$_i$ or reference image 12$_i$ and 12$_{i+1}$ should be within an image viewing area 30 located directly in front of the user 26. This configuration insures the most uniformly lit and lowest flare lighting conditions as taught in the present invention.

All of the reference images 12 and the test image 14 and their associated holders 10, 16, and 18 are mounted or supported on a neutral angled drafting table 20. The neutral angled drafting table 20 was chosen as a solid support and is easily tilted to an appropriate angle to achieve the proper lighting conditions taught in the present invention. The reference image holder guide 18 is solidly attached to the neutral angled drafting table 20. The neutral angled drafting table 20 is painted a neutral, 18% gray in the preferred embodiment of the present invention. To correctly position the user 26 for viewing the test images in the image viewing area 30, a viewing distance constraint 24 in the form of a headrest is positioned by a viewing distance constraint support 22. The viewing distance constraint support 22 is attached to the to the neutral angled drafting table 20. Illumination for viewing the test image 14 and reference images 12 is provided by a light source 28, mounted above the user 26 and neutral angled drafting table 20. The light source 28 uniformly illuminates the test image 14 and the reference images 12 when they are disposed in the image viewing area 30 for viewing by a user.

Also shown in FIG. 1 is a more detailed view of the reference image holder 10 in an exploded fashion. As the user 26 makes a visual assessment using the apparatus of taught in the present invention, the user 26 slides the reference image holder 10 right and left to position directly below the test image 14, the reference image 12$_i$ that most nearly matches the overall image quality of the test image 14, or alternatively if one of the reference images is not of exactly the same overall image quality, slides the reference image holder such that the two reference images 12$_i$ and 12$_{i+1}$ that bracket the test image 14 in overall image quality are below the test image 14. The reference image holder 10 has a series of numbers that visually indicates the numerical representations of overall image quality 34 that correspond to the reference images 12. The user 26 then records the numerical representation of overall image quality 34 corresponding to the reference image 12$_i$ with identical overall image quality of the test image 14. If the overall image quality of the test image 14 is determined to lie between two of the reference images 12$_i$ and 12$_{i+1}$, the nearest of the intermediate numerical representations of overall image quality 38 is reported as the visual assessment of the numerical representation of the overall image quality of the test image 14. Should the overall image quality of the test image 14 be greater than the overall image quality of the highest overall image quality reference image 12$_1$ or lower than the overall image quality of the reference image with the lowest image quality 12$_n$, the user reports an estimate of the extrapolated numerical representation of overall image quality 36 as the visual assessment.

Figure 2:
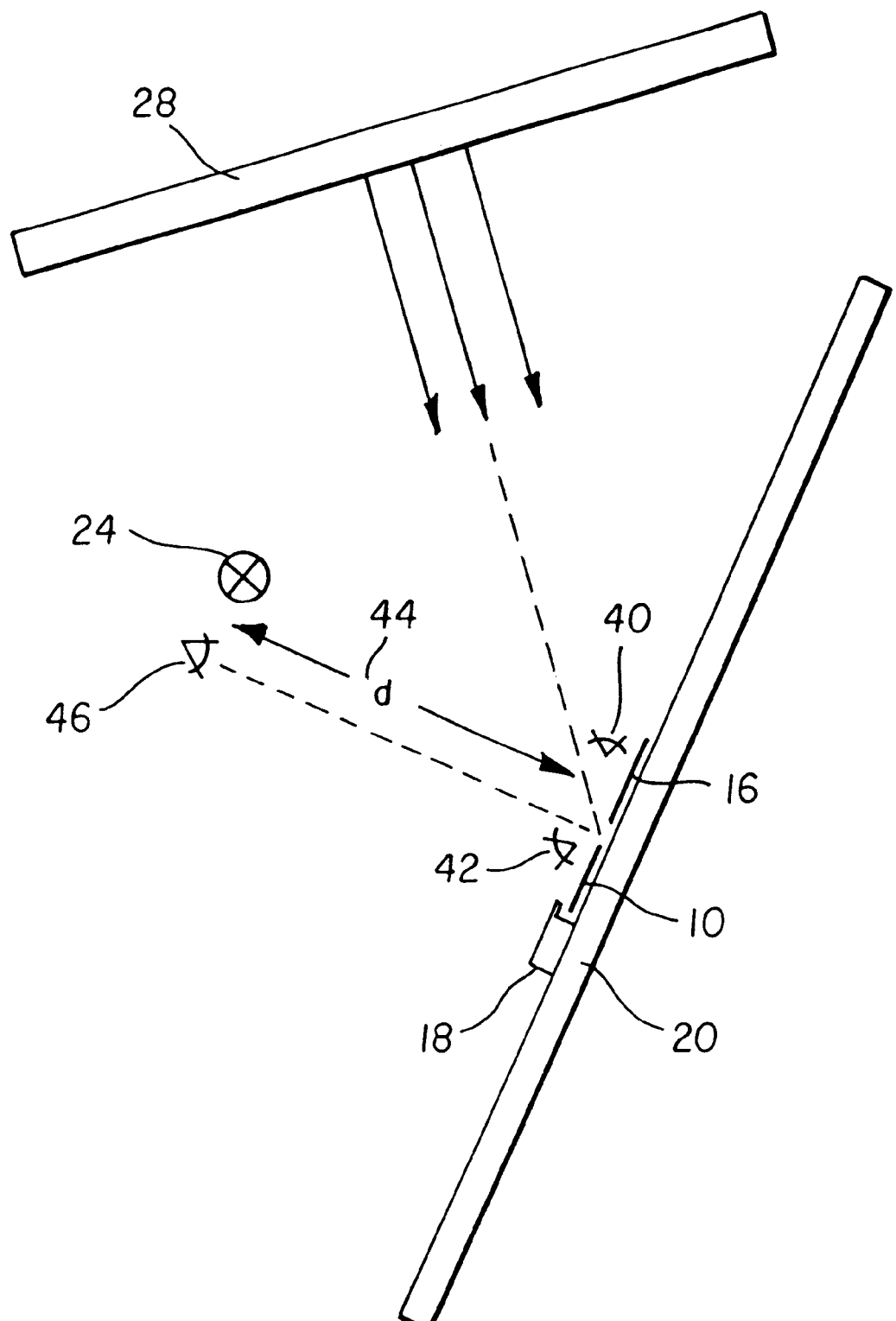
FIG. 2 is a cross-sectional schematic showing the geometrical and spatial relationship of the viewing environment and apparatus.

Referring to FIG. 2, this cross-sectional schematic shows the geometrical and spatial relationships of the light source 28 and the image containing components of the viewing environment. Specifically the light source 28 is positioned such that the partially collimated light from a D5000 fluorescent source falls on the test image 14 and reference images 12 at an incident angle of forty-five degrees 40 to the normal to the surface of the images. The user's 26 head is constrained by the viewing distance constraint 24 such that the eye is positioned 46 at a specified viewing distance 44 for the image size chosen for the test image 14 and the reference images 12 at a normal (zero degrees) viewing angle 42. The neutral angled drafting table 20 is adjusted such that the desired incident light angle of forty-five degrees 40 and zero degree viewing angle 42 are achieved.

Figure 3:
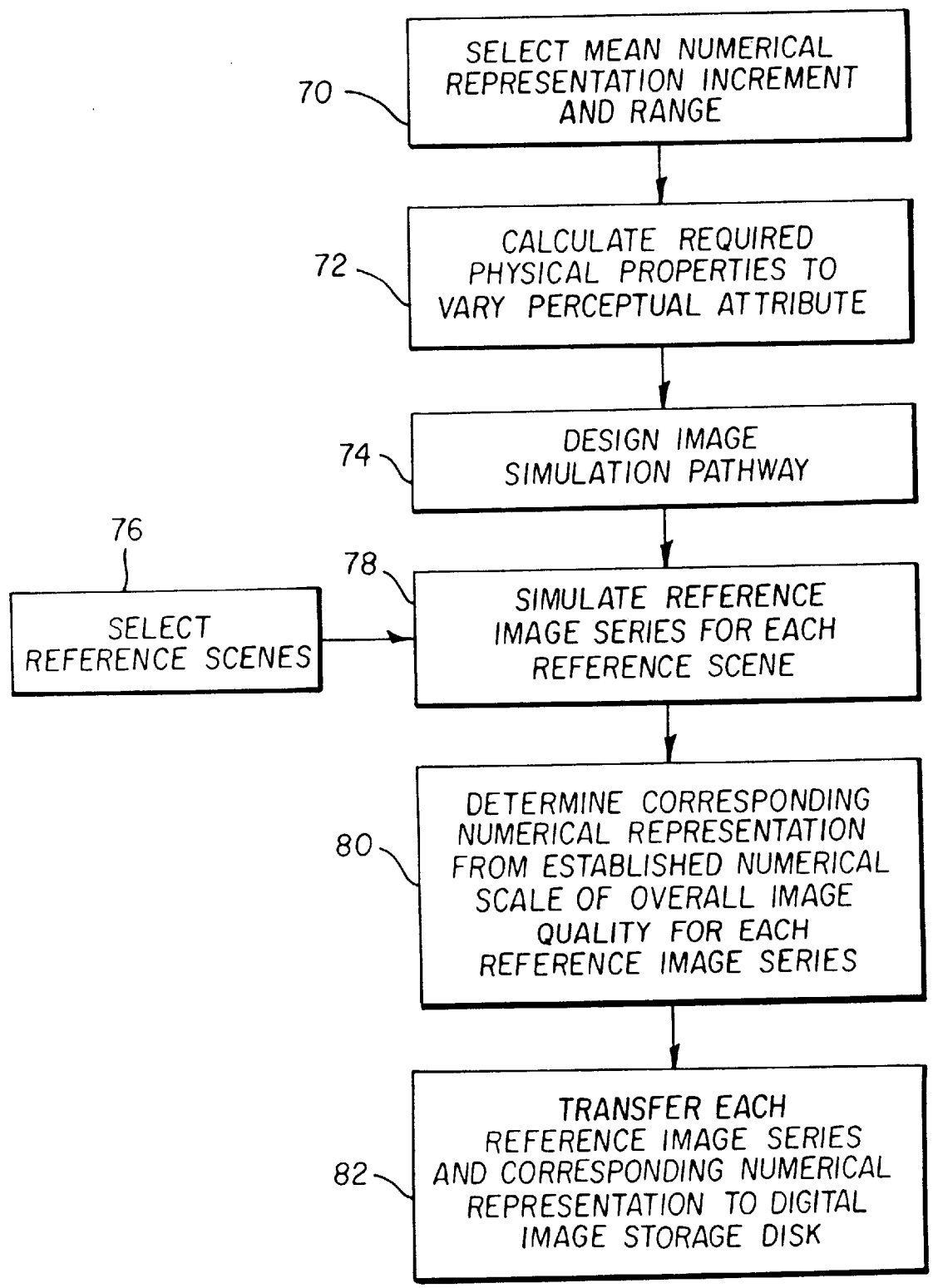
FIG. 3 is a flowchart showing one way of creating a reference image series the members of which vary from each other by at least one perceptual attribute and wherein each reference image has a corresponding numerical representation of overall image quality.

The reference image series 12 is most conveniently produced through the use of digital image simulation using techniques well known in the art. However, the simulation of the necessary reference image series 12 requires a precise application of standard digital image simulation techniques according to the method taught in FIG. 3. The first step in producing a reference image series is to select the numerical representation increment and range 70. The increments selected for the numerical representation should be perceptually uniform or slowly varying. In the preferred embodiment it was found particularly advantageous to have the increments of the numerical representation approximately equal to three (3) just noticeable differences of overall quality. This facilitates a desirable combination of speed and precision for the user because the reference images clearly differ in overall image quality and the user can easily interpolate to intermediate numerical representations. The range of the reference image series should slightly exceed the expected range of overall image quality exhibited by the test images to be assessed using the method of the present invention.

Given the selected numerical representation increment and range 70, the physical properties required to vary the perceptual attribute under consideration in the reference image series are calculated in block 72. In the preferred embodiment, where the perceptual attribute varied is image sharpness, the modulation transfer function of the reference image necessary to produce images with the desired numerical representation increment and range selected 70 would be calculated. An image simulation pathway is then designed 74 to produce the reference image series. In the preferred embodiment disclosed in the present invention, the modulation transfer function of the reference images is changed through the use of digital spatial filters introduced in the image simulation pathway in a manner well known in the art.

The next step in block 76 is to select the reference scenes to be used in each of the reference image series. The reference scenes of block 76 do not need to be the same scenes as the depicted in the test images. A comparison was made between the accuracy and precision in situations where the scenes depicted in the test images are and are not the same as those in the references image series. The precision and accuracy of the numerical representation of the overall image quality was found to be identical. If the numerical representation of a wide variety of test images 14 of many different scenes is going to be determined using this method, it is best to prepare a number of reference image series for use in making the visual assessments. Users are generally more comfortable and confident making visual assessments when the test image 14 and the reference image 12 are of the same general type, i.e. indoor flash, outdoor scenic, outdoor group, indoor public building, or any other general categories.

Given the selection of the reference scenes in block 76, a digital image simulation pathway in block 74 is used to simulate a reference image series 78 for each increment over the range of the numerical representation determined in 70. This is done for each reference scene selected 74. The term digital image simulation pathway means a series of digital processing steps performed to yield images with desired properties. These steps are well known and will suggest themselves to those skilled in the art.

At this point, the numerical representations associated with each of reference images 12 in the reference image series 78 are those corresponding to an average scene having the specified physical properties 72. To further extend this method to permit scene specific calibration of each reference image series 78, each unknown scene is individually calibrated to accommodate scene content effects 80. This is done by cross-comparison of the selected reference scenes to standard scenes containing the same perceptual attribute. The standard scenes are calibrated by trained expert judges using special standards under prescribed viewing conditions. Preferably, a high sharpness and a low sharpness reference image of a number of scenes of known modulation transfer function and known numerical representation produced using the image simulation pathway 74 are cross compared to reference images produced using the same simulation pathway 74 for each of the reference scenes selected in 76. Once an unknown scene that suffers the same change in overall image quality as a scene with a known relationship between the modulation transfer function and the numerical representation, the numerical representation associated with the known scene is assigned to the unknown scene. This process is repeated to calibrate all unknown scenes. Following the calibration of each series of reference images, the reference images are mounted in a reference image holder for use and the corresponding numerical representation recorded for use in the final data analysis.

In practice, the user slides the reference image holder along the reference image holder guide 18 until the overall image quality of the reference images 12 and test image 14 within the image viewing area 30 are of comparable overall image quality. A user now compares the reference image 12 with the test image 14 in the image viewing area 30 for determining the relationship of the overall image quality of the most similar reference images 12 to that of the test image and the numerical representation of the test image are inferred and recordable. The final determination of the numerical representation is assessed by selecting and reporting the numerical representation of overall image quality 34 from those inscribed on the reference image holder 10. Following the determination of the numerical representation for a test image 14, the user records the numerical representation along with the documentation identifying the nature of the test image for subsequent analysis.

The invention has been described in detail with particular reference to certain preferred embodiments thereof, but it will be understood that variations and modifications can be effected within the spirit and scope of the invention.

PARTS LIST 10 reference image holder
12 reference images
$12_1$ $1^{st}$ reference image
$12_2$ $2^{nd}$ reference image
$12_i$ $i^{th}$ reference image
$12_n$ $n^{th}$ reference image
14 test image
16 test image holder
18 reference image holder guide
20 neutral angled drafting table
22 viewing distance constraint support
24 viewing distance constraint
26 user
28 light source
30 image viewing area
32 direction sliding motion of reference image holder
34 numerical representation of overall image quality
36 extrapolated numerical representation of overall image quality
38 intermediate numerical representations of overall image quality
40 incident angle of forty-five degrees
42 zero degree viewing angle
44 nominal hand held viewing distance
46 user's eye position
70 mean numerical representation increment and range
72 calculate physical properties
74 design image simulation pathway
76 select reference scenes
78 simulate reference image series
80 determine corresponding numerical representation
82 transfer each reference image series

What is claimed is:

1. An apparatus for producing a numerical representation of user perceived overall image quality of a test image, comprising:

(a) a viewing support for mounting the test image;

(b) a reference image holder disposed relative to the test image on the viewing support, the reference image holder mounting a reference image series in which each reference image differs from each other reference image by at least one perceptual attribute, wherein each reference image has a corresponding numerical representation indicating overall image quality, the reference image holder being movable so that any one of the reference images can be disposed in a viewing position adjacent to the test image; and (c) a source of light for uniformly illuminating both the test image and the reference image disposed at the viewing position for viewing by a user, such that a user compares a reference image with the test image at the viewing position to determine a relationship between the overall image quality of the most similar reference images to the overall image quality of the test image, infers a numerical representation of the overall image quality of the test image, the numerical representation being recordable.

2. The apparatus of claim 1 wherein the reference image holder visually indicates the numerical representations that correspond to the reference images.

3. The apparatus of claim 2 further comprising a guide having a track, the reference image holder being slidably mounted in the track of the guide.

* * * * *